(12) United States Patent
Booker et al.

(10) Patent No.: US 10,188,412 B2
(45) Date of Patent: Jan. 29, 2019

(54) SNARE AUTO MICRO-LOCK

(71) Applicant: COOK MEDICAL TECHNOLOGIES LLC, Bloomington, IN (US)

(72) Inventors: Robert Booker, Vandergrift, PA (US); Louis B. Goode, Cranberry Township, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 192 days.

(21) Appl. No.: 15/095,464

(22) Filed: Apr. 11, 2016

(65) Prior Publication Data

US 2016/0345989 A1    Dec. 1, 2016

Related U.S. Application Data

(60) Provisional application No. 62/169,287, filed on Jun. 1, 2015.

(51) Int. Cl.
*A61B 17/00* (2006.01)
*A61B 17/221* (2006.01)
*A61B 17/29* (2006.01)

(52) U.S. Cl.
CPC .... *A61B 17/221* (2013.01); *A61B 2017/0042* (2013.01); *A61B 2017/00358* (2013.01); *A61B 2017/00858* (2013.01); *A61B 2017/2212* (2013.01); *A61B 2017/2924* (2013.01); *A61B 2017/2946* (2013.01)

(58) Field of Classification Search
CPC ........ A61B 17/221; A61B 2017/00358; A61B 2017/0042; A61B 2017/00858; A61B 2017/2212; A61B 2017/2924; A61B 2017/2946; A61B 2017/2217
See application file for complete search history.

(56) References Cited

U.S. PATENT DOCUMENTS

| | | | | |
|---|---|---|---|---|
| 5,171,233 A | * | 12/1992 | Amplatz | A61B 17/221 604/540 |
| 5,522,819 A | | 6/1996 | Graves et al. | |
| 2004/0111082 A1 | * | 6/2004 | Howell | A61B 17/221 606/2.5 |

(Continued)

OTHER PUBLICATIONS

International Search Report and Written Opinion for related application No. PCT/US2016/026103 (12 pgs).

(Continued)

*Primary Examiner* — Katrina M Stransky
(74) *Attorney, Agent, or Firm* — Brinks Gilson & Lione

(57) ABSTRACT

A surgical snare is provided having an operating wire and an outer sheath having a lumen extending therethrough, wherein the operating wire is disposed within the lumen and is longitudinally movable within the lumen. The surgical snare also has a first locking member attached to the operating wire and a second locking member attached to the outer sheath. The first locking member is frictionally engageable with the second locking member by sliding the outer sheath longitudinally along the operating wire until the first locking member contacts the second locking member. The operating wire is prevented from moving longitudinally with respect to the outer sheath when the first locking member is frictionally engaged with the second locking member.

20 Claims, 5 Drawing Sheets

(56) References Cited

U.S. PATENT DOCUMENTS

| | | |
|---|---|---|
| 2010/0057110 A1 | 3/2010 | Lampropoulos et al. |
| 2011/0301619 A1 | 12/2011 | Walters |
| 2012/0004647 A1* | 1/2012 | Cowley ............ A61B 17/00234 |
| | | 606/1 |
| 2013/0046297 A1 | 2/2013 | Lingeman et al. |
| 2014/0249569 A1 | 9/2014 | Kusleika |

OTHER PUBLICATIONS

International Search Report and Written Opinion for related application No. PCT/US2016/026103 dated Jun. 16, 2016 (14 pgs).

\* cited by examiner

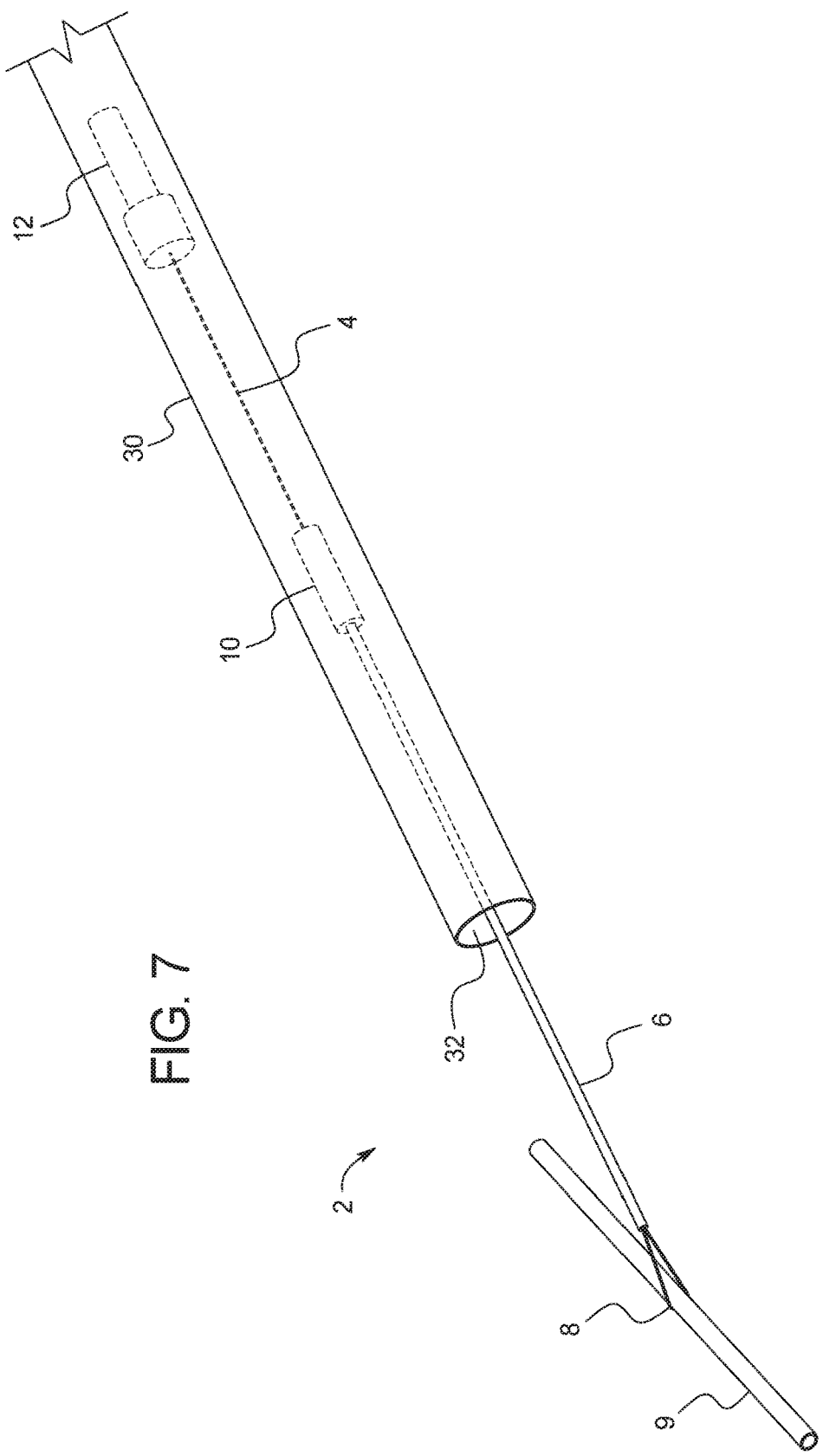

SNARE AUTO MICRO-LOCK

CROSS-REFERENCE TO RELATED APPLICATIONS

The present patent document claims the benefit of the filing date under 35 U.S.C § 119(e) of Provisional U.S. Patent Application Ser. No. 62/169,287 filed Jun. 1, 2015, which is hereby incorporated by reference.

FIELD

The present disclosure relates generally to medical devices, and more specifically to surgical snares.

BACKGROUND

The statements in this section merely provide background information related to the present disclosure and may not constitute prior art.

Medical devices of various shapes and sizes are commonly placed within patients to repair or assist in repairing damaged portions of the body. Often, these medical devices need to be removed from the patient at some point. For example, the patient may no longer need the medical device or the device is damaged and must be replaced. If these medical devices are not removed, they may cause harm to the patient, such as by causing infections or blockage in various body lumens.

However, removing these medical devices from a patient by performing open surgery is not ideal. The cost and time, both to perform the surgery and for the patient to recover, are prohibitive. Additionally, these patients are often in weakened states and are thus more susceptible to additional complications from performing an unnecessary open surgery.

Thus, minimally invasive techniques are preferable to performing open surgery. Frequently, a surgical snare is used to remove a medical device from a patient's body. Surgical snares are long, flexible devices that are inserted into a patient's body lumen. Generally, the distal end of the surgical snare uses some type of capture mechanism to secure the medical device to the surgical snare. Once the medical device is secured to the surgical snare, the surgical snare may be retracted from the patient's body, pulling the medical device with it.

Surgical snares as currently designed have several disadvantages. Often, the snares require the constant use of both of the surgeon's hands to properly manipulate the snare and remove the medical device from the body. Using both hands can be cumbersome and can lead to accidental disengagement of the surgical snare from the medical device during the removal process since both hands may be needed to maintain the snare in a closed configuration about the medical device. Additionally, most surgical snares have large, clunky handles that the surgeon uses to manipulate the capture mechanism of the snare. In addition to being cumbersome, these handles also inhibit the introduction of a larger retrieval catheter over the surgical snare. Larger retrieval catheters are often required when attempting to extract large medical devices from a patient's body.

SUMMARY

In one form of the present disclosure, a surgical snare is provided comprising an operating wire and an outer sheath comprising a lumen extending therethrough, wherein the operating wire is disposed within the lumen. Also, a frictional locking member is operably coupled to the outer sheath, wherein the frictional locking member prevents longitudinal movement of the operating wire with respect to the outer sheath when no external force is applied, but allows longitudinal movement of the operating wire within the outer sheath when an external force is applied. Additionally, the longitudinal movement of the operating wire with respect to the outer sheath may be prevented by frictional forces between the frictional locking member and the operating wire. The frictional locking member may comprise a helical wire wrapped around flexible tubing or a rigid tube comprising at least one crimp. The surgical snare may also have the operating wire comprise an expandable loop at a distal end of the operating wire. The surgical snare may also comprise a handle attached to a proximal end of the operating wire. The surgical snare may also comprise a retrieval catheter comprising a catheter lumen, wherein the outer sheath and frictional locking member are movably disposed within the catheter lumen.

In another form of the present disclosure, a retrieval device is provided comprising a retrieval member, a tube comprising a channel therethrough, the channel receiving the retrieval member, and a fastening member operably coupled to the tube. Additionally, the fastening member frictionally engages with the retrieval member, thereby preventing longitudinal movement of the retrieval member along the channel of the tube when no external force is applied. The retrieval device may also comprise a handle attached to a proximal end of the tube. The retrieval device may also further comprise a catheter comprising a lumen, wherein the tube and the fastening member are disposed within the lumen.

In still another form of the present disclosure, a method for retrieving a medical device is provided. The method comprises providing a surgical snare comprising an operating wire comprising an expandable loop at a distal end of the operating wire, an outer sheath comprising a lumen extending therethrough, the operating wire disposed within the lumen and longitudinally movable within the lumen, and a locking member operably coupled to the sheath. The method further comprises inserting the surgical snare into a patient's body with the expandable loop in a released state and feeding the surgical snare into the patient's body until the expandable loop is adjacent to the medical device. The method further comprises securing the expandable loop around the medical device by sliding the outer sheath along the operating wire until the expandable loop is in an engaged state, wherein the expandable loop has a smaller circumference while in the engaged state than when the expandable loop is in the released state. Further, the locking member frictionally engages the operating wire to thereby maintain the expandable loop in the engaged state without providing an external force. The method may further comprise retracting the surgical snare and the medical device from the patient's body. The method may alternatively comprise providing a retrieval sheath comprising a retrieval sheath lumen, feeding the retrieval sheath over the surgical snare by placing the surgical snare within the retrieval sheath lumen until the medical device is within a distal portion of the retrieval sheath lumen, and retracting the surgical snare and the medical device through the retrieval sheath lumen from the patient's body.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 7 is a drawing of a surgical snare with a retrieval catheter.

DETAILED DESCRIPTION

Figure 1:
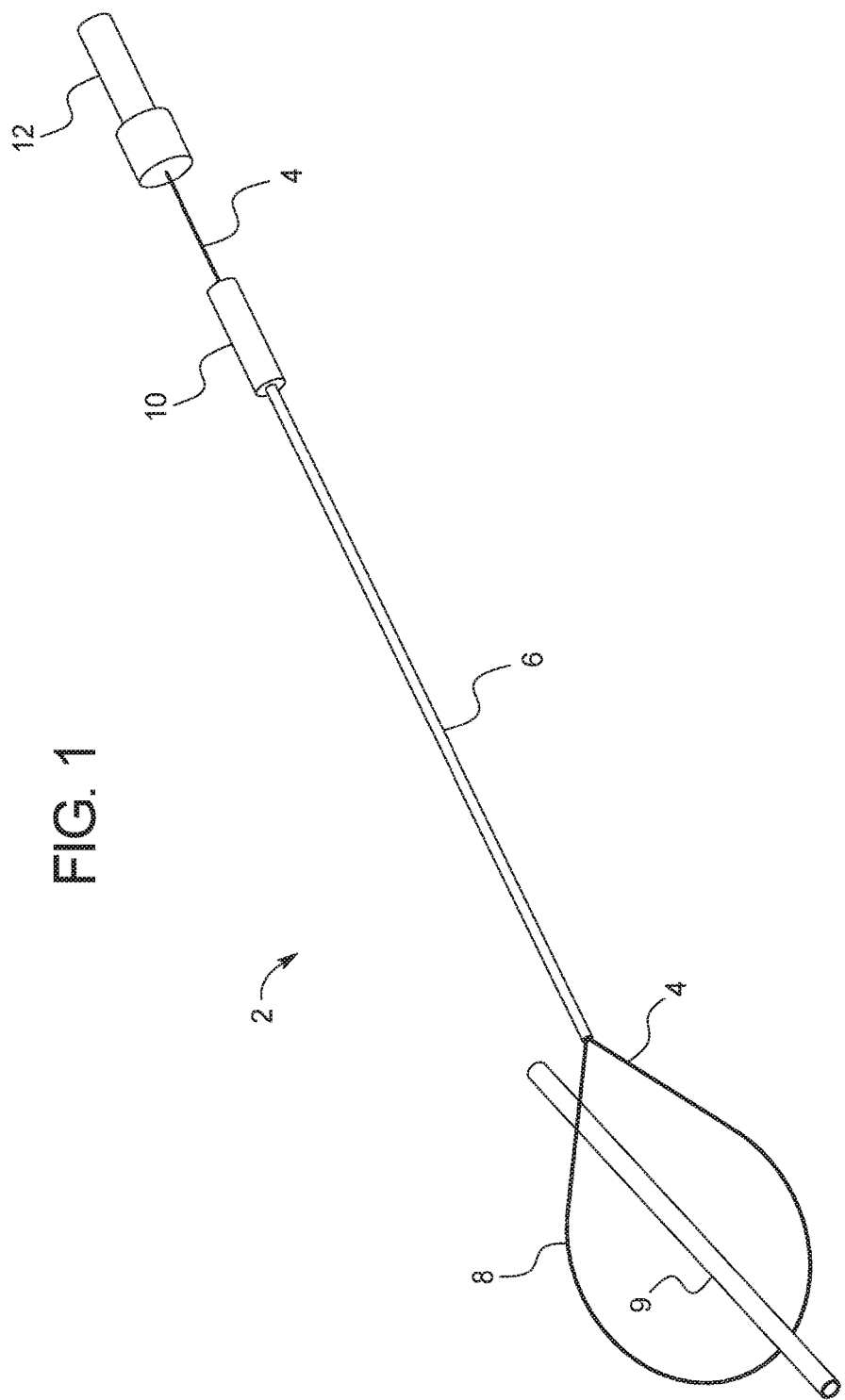
FIG. 1 is a drawing of a surgical snare with an operating wire in a released state.

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed with the present disclosure. The cross-hatching patterns are merely exemplary of preferable materials or are used to distinguish between adjacent or mating components illustrated within the drawings for purposes of clarity.

Figure 2:
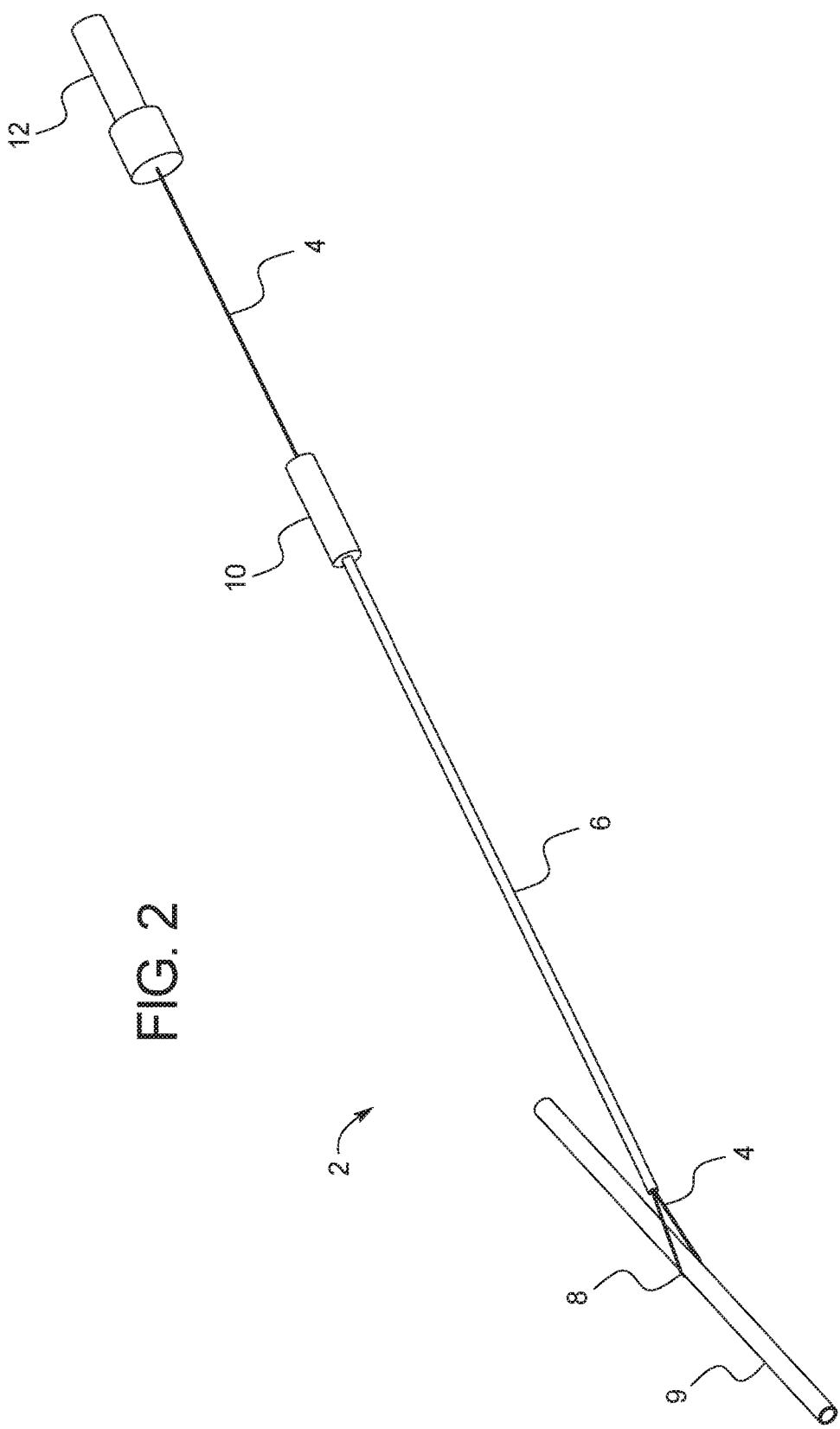
FIG. 2 is a drawing of a surgical snare with an operating wire in an engaged state.

FIGS. 1 and 2 show a surgical snare 2. FIG. 1 shows the surgical snare 2 in a released or fully expanded (open) state, while FIG. 2 shows the surgical snare 2 in an engaged or partially contracted (closed) state. The surgical snare 2 has an operating wire 4 and an outer sheath 6. The operating wire 4 is ideally made of a flexible, compliant, biocompatible material such as, but not limited to, stainless steel. The outer sheath 6 is ideally made of a flexible, biocompatible material such as, but not limited to, teflon. A portion of the operating wire 4 is disposed within a lumen (not shown) of the outer sheath 6, and the operating wire 4 is longitudinally movable within the lumen. An expandable loop 8 may be on the distal end of the operating wire 4. A locking member 10 is operably coupled with the outer sheath 6. In this embodiment, the locking member 10 is a tube with a channel through which the operating wire 4 is movably disposed. The locking member 10 may be fixedly attached to the outer sheath 6. Alternatively, the locking member 10 may be disposed adjacent to a proximal end thereof, thus making the locking member 10 and outer sheath 6 individually slidable along the operating wire 4. Additionally, the locking member 10 may be integrally formed with the outer sheath 6, wherein the outer sheath 6 and locking member 10 are one piece. The surgical snare 2 may also include a handle 12. The handle 12 may be attached to the operating wire 4 to assist the physician in manipulating the operating wire 4 relative to the outer sheath 6.

The surgical snare 2 can alternate between a released state (FIG. 1) and an engaged state (FIG. 2). When in the released state, the circumference of the expandable loop 8 is larger than when the surgical snare 2 is in the engaged state. The surgical snare 2 is changed from the released state to the engaged state by pushing the outer sheath 6 in a distal direction relative to the operating wire 4 while pulling the operating wire 4 in a proximal direction relative to the outer sheath 6. As the outer sheath 6 and operating wire 4 are pulled in opposite directions, the distal end of the outer sheath 6 will reach the expandable loop 8. A portion of the expandable loop 8 will eventually be pulled into the lumen of the outer sheath 6 and the expandable loop 8 will start to contract, thus decreasing the circumference. Eventually, as the outer sheath 6 and operating wire 4 continue to be pulled in opposite directions, the expandable loop 8 will contract to a point where the surgical snare 2 is in the engaged state as shown in FIG. 2. The surgical snare 2 is ideally in the engaged state when inserted into a body lumen to prevent the expandable loop 8 from damaging or catching on the walls of the body lumen. Alternatively, the expandable loop 8 may be retracted so that the entire expandable loop 8 is within a distal portion of the outer sheath 6, thus minimizing any damage to the walls of the body lumen.

Generally, during the engaged state the surgical snare 2 has captured a medical device 9 that is located within a patient's body. FIGS. 1 and 2 show the medical device 9 as a small catheter, however the surgical snare 2 can be used to retrieve various other medical devices including, but not limited to, a feeding tube, pacemaker lead, and stent. Additionally, the surgical snare 2 may be used to capture and remove gall stones, kidney stones or other objects that must be removed from a patient's body. The surgical snare 2 then must remain in the engaged state as the medical device 9 is retracted from the patient's body. However, the expandable loop 8 is generally manufactured so that it tends to elastically revert back to the released state when no external forces are applied. Thus, as is the case with current surgical snares, if the physician loses the grip on either the operating wire 4 or the outer sheath 6, the expandable loop 8 will automatically expand back to the released position and lose capture of the medical device 9. To prevent accidental release of the medical device 9, the present invention includes a locking member 10 to maintain the surgical snare 2 in an engaged state without the physician having to apply any forces to the operating wire 4 or outer sheath 6.

Figure 3:
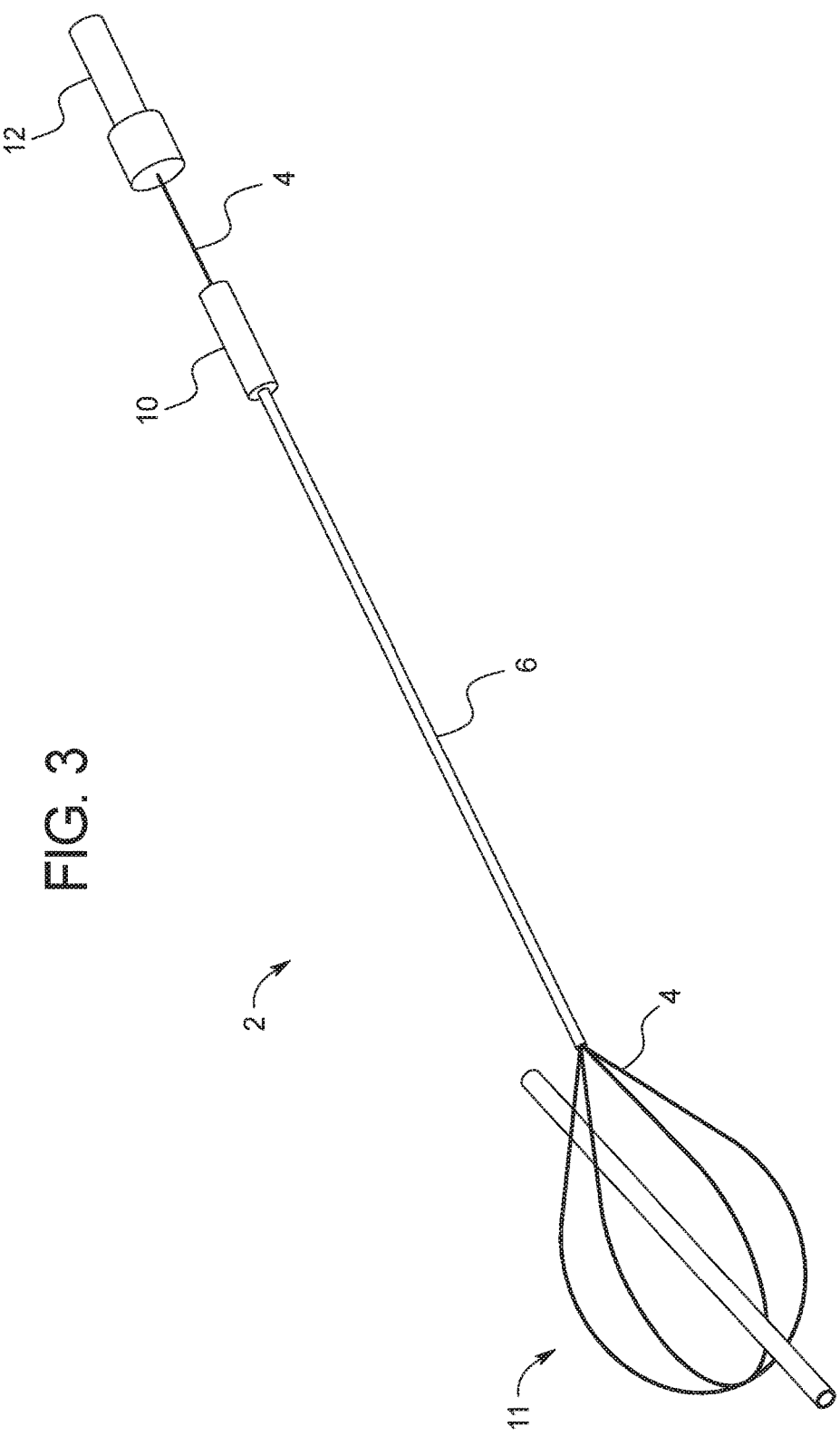
FIG. 3 is a drawing of a surgical snare with a basket in a released state.

While the embodiment of FIGS. 1 and 2 show an expandable loop 8 at the proximal end of the operating wire 4, other devices well known in the art can be substituted for the expandable loop 8 including, but not limited to, a basket. As shown in FIG. 3, a basket 11 replaces the expandable loop 8 at the distal end of the operating wire 4. Rather than a simple loop as shown with the expandable loop 8, a basket 11 may have additional loops to ensure a more secure capture of the medical device 9. FIG. 3 shows the basket 11 with two loops; however additional loops with various shapes or patterns may be used to ensure a more secure capture of the medical device 9. The basket 11 functions similarly to the expandable loop 8. As the outer sheath 6 is moved distally relative to the operating wire 4, the loops of the basket 11 contract, thus securing the medical device 9 within the basket 11.

Figure 4:
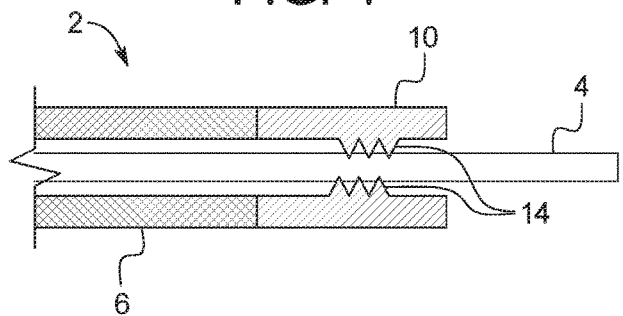
FIG. 4 is a detailed view of one embodiment of the locking member.

FIG. 4 shows a detailed cross-sectional view of one potential embodiment of the locking member 10. Several teeth or ridges 14 may extend into the channel 16 of the locking member 10. These ridges 14 contact the operating wire 4 and apply a frictional force thereto that is sufficient to inhibit movement of the operating wire 4. As described above, when the surgical snare 2 is in the engaged state, the operating wire 4 tends to revert back into the released state or the tension force applied by the snare will tend to naturally ease or loosen. However, the ridges 14 of the locking member 10 create a frictional force against the operating wire 4 that is great enough to prevent the operating wire 4 from moving relative to the outer sheath 6 once the handle is released by the user. Thus, the locking member 10 retains the surgical snare 2 in the engaged state without the physician having to maintain a constant grip on both the operating wire 4 and the outer sheath 6. The locking member 10 allows the physician to capture and remove the medical device 9 from a patient's body without fear of losing capture during retraction of the surgical snare 2. However, the frictional forces between the operating wire 4 and the locking member 10 are not so great as to prevent the physician from manually moving the surgical snare 2 between an engaged and a released state. When the physician applies an external force to the operating wire 4 and the outer sheath 6, the locking member 10 will still permit the operating wire 4 to longitudinally move relative to the outer sheath 6. The frictional forces need to be great enough to overcome the expandable loop 8 tending towards a released state, but not so great as to prevent intentional manipulation by the physician.

While the ridges 14 shown in FIG. 4 have jagged edges, other shapes can be used to create friction between the operating wire 4 and the locking member 10. For example, rounded bumps may also be used. Additionally, the ridges 14 may be made of a variety of materials, including, but not limited to, compressible rubbers and pliable plastics such as silicone or PVC. Ridges 14 may also be created by placing compressible tubing into inner lumen of locking member 10 then installing crimps into locking member 10 to create desired friction between compressible tube and operating wire 4. The ridges 14 may also be made of a tacky or adhesive material to increase the friction between the locking member 10 and operating wire 4. The ridges 14 may be made entirely of an adhesive material, or the adhesive material may be coated on the surfaces of the ridges 14 that contact the operating wire 4.

Figure 5A:
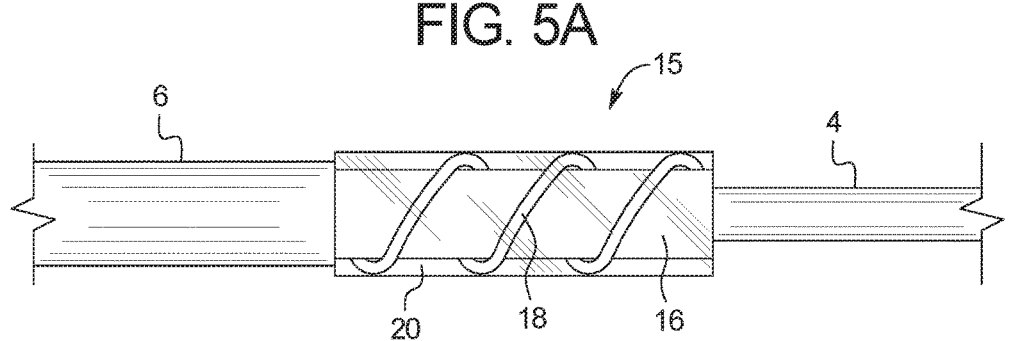
FIG. 5A is a detailed view of another embodiment of the locking member.
Figure 5B:
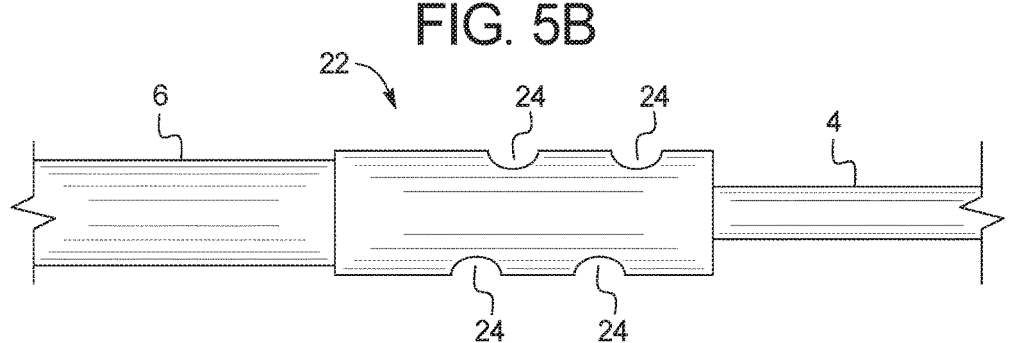
FIG. 5B is a detailed view of another embodiment of the locking member.

While FIG. 4 shows the locking member 10 with ridges 14 to create the friction between the operating wire 4 and the locking member 10, any number of ways to create a sufficient amount of friction may be used. FIGS. 5A and 5B show two other exemplary embodiments of the locking member 10. FIG. 5A shows a locking member 15 composed of three layers. The locking member 15 is generally tubular in shape with a channel through which the operating wire 4 runs. The inner layer of the locking member 15 is a first flexible tube 16, preferably made of silicone, although other materials may be used. The middle layer is a wire 18 wrapped helically around the flexible tube 16. The wire 18 is ideally made of a harder material, such as a biocompatible metal, although other materials may be used. The outer layer of the locking member 15 is a second flexible tube 20 that is used to confine the wire 18. While the second flexible tube 20 is also ideally made of silicone, other materials may be used. The wire 18 provides ridges on the inner surface of the locking member's channel which contact the operating wire 4. These ridges create friction between the operating wire 4 and the locking member 15, thus achieving a similar locking result as described above.

FIG. 5B shows another potential locking member 22. The locking member 22 is made of a hard, non-compliant material such as stainless steel, but other materials may be used. Several crimps 24 are created on the locking member that decreases the circumference of the lumen of the locking member in those regions. The decreased circumference in those areas causes increased contact between the locking member 22 and the operating wire 4. The increased contact increases the frictional forces between the locking member 22 and the operating wire 4 which allows the surgical snare 2 to remain in the engaged state without applying any external forces.

The locking member 10 does not need to be located at the proximal end of the outer sheath 6 as shown in FIGS. 1 and 2. For example, the locking member may instead be located at the distal end of the outer sheath 6, or even in the middle of the outer sheath 6. Additionally, the locking member 10 does not need to be a separate and distinct component from the outer sheath 6. For example, the locking member 10 in FIG. 4 may be removed from the surgical snare 2 and the ridges 14 may be placed within the lumen of the outer sheath 6. Thus, the requisite frictional forces are still being created to prevent longitudinal movement of the operating wire 4 within the outer sheath 6, while eliminating the need for a separate locking device.

Figure 6:
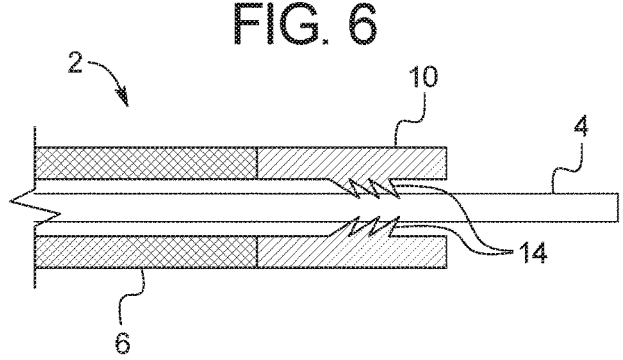
FIG. 6 is a detailed view of an alternative embodiment of the locking member.

In the embodiments discussed above, the frictional forces created by the locking member 10 are similar when the surgical snare 2 is being released and when the surgical snare 2 is being engaged. However, the locking member 10 may be designed to apply differing frictional forces to the operating wire 4 when it is moved in different directions relative to the outer sheath 6. In other words, the locking member 10 may be designed to have a uni-directional coefficient of friction. For example, FIG. 6 shows a locking member 10 similar to the locking member 10 in FIG. 4. However, in this embodiment, the ridges 14 are resilient flaps angled in a proximal direction. With this design, the ridges 14 compress against the inside wall of the locking member 10 when the operating wire 4 is moved proximally relative to the outer sheath 6. However, once proximal movement of the operating wire 4 ceases, the ridges 14 spring outwardly to engage the operating wire 4 and prevent distal movement, thus maintaining the surgical snare 2 in the engaged state without the physician applying any external forces. Designing the ridges 14 in this way lowers the friction between the operating wire 4 and the locking member 10 while the operating wire 4 is manipulated from the released state to the engaged state, thus allowing the physician to more easily manipulate the surgical snare 2 from the released state to the engaged state, while still maintaining the advantages of the automatic locking member 10.

While a constant diameter operating wire 4 is commonly used with surgical snares, a varying diameter operating wire 4 may also be used in the present invention. With a varying diameter operating wire 4, a portion of the operating wire 4 may have a small enough diameter such that the locking member 10 will not cause a significant amount of friction between the locking member 10 and the operating wire 4. The smaller diameter portion of the operating wire allows the surgical snare to be easily manipulated without the increased friction caused by the locking member 10. However, the operating wire 4 may also have a larger diameter for a portion of its length that corresponds to when the surgical snare 2 is in the engaged state. Because this portion of the operating wire 4 has a larger diameter, it will engage with the locking member 10 and create the requisite frictional forces necessary to retain the surgical snare 2 in the engaged state.

In some instances, a surgical snare alone is insufficient to successfully remove a medical device from a patient's body. For example, when a larger medical device, such as a pacemaker lead, needs to be removed from a patient's body, a retrieval catheter must be used in addition to the surgical snare 2 described above. In FIG. 7, a retrieval catheter 30 is shown with a lumen 32. The retrieval catheter 30 is large enough to fit the entire surgical snare 2 within its lumen 32. In practice, the retrieval catheter 30 is used in conjunction with the surgical snare 2. First, as described in more detail above, the surgical snare 2 is inserted into the patient's body and manipulated so that the expandable loop 8 captures the medical device 9. At this point, the retrieval catheter 30 is inserted over the surgical snare 2 and into the patient's body until the medical device 9 is within a distal portion of the lumen 32. The surgical snare 2, along with the medical device 9, can then be retracted from the patient through the lumen 32 of the retrieval catheter 30. The retrieval catheter 30 remains within the patient's body during the retraction process to provide a contained and secure passageway for the medical device 9 to be retracted. Often, body tissue has grown onto and about the medical device 9. Thus, the retrieval catheter 30 may also include a cutting member on the distal end of the retrieval catheter 30 to disrupt or cut the tissue that has grown around the medical device 9. The cutting member is typically tubular in shape with scallops or helical ridges about the outside of the cutting member. Alternatively, the retrieval catheter 30 may be inserted into the patient's body lumen prior to the surgical snare 2. The surgical snare 2 can then be guided through the retrieval catheter's lumen 32 to where the medical device 9 is located.

Without the assistance of the retrieval catheter 30, there would be a greater risk of damage to body tissue as the medical device 9 is retracted. For example, a larger medical device may bump or scrape the walls of the body lumen from which it is being retracted. In addition to damage to the patient's body, this unwanted bumping and scraping may also cause the surgical snare 2 to lose capture of the medical device 9. Thus a retrieval catheter 30 is often advantageous when extracting a medical device from a patient's body by using a surgical snare 2.

However, retrieval catheters are difficult to use with conventional surgical snares. Surgical snares often have large, bulky handles that allow the physician to manipulate the surgical snare with one or two hands. These larger handles cannot fit within the lumen of the retrieval catheter. Thus, the handles must be removed before inserting the retrieval catheter. During removal of the handle, the surgical snare might accidentally lose capture of the medical device. Additionally, the physician will eventually have to release the grip on either the outer sheath or the operating wire of the surgical snare as the retrieval catheter is inserted over the surgical snare. When the physician releases the grip, the surgical snare may once again lose capture of the medical device. The present invention eliminates these problems. The handle 12 and the locking member 10 can be designed to be low profile members with small circumferences, thus allowing the retrieval catheter 30 to be easily fed over the entire surgical snare 2 without needing to remove the handle 12. Additionally, the automatic locking member 10 secures the surgical snare 2 in the engaged state without the physician having to maintain contact with the surgical snare 2. Thus, the retrieval catheter 30 can be fed over the surgical snare 2 without fear of losing capture of the medical device 9. In one example, the handle 12 may include a rigid tube that is crimped, or otherwise mechanically attached, to the operating wire 4 near the proximal end of the operating wire 4. Alternatively, instead of using the handle 12 shown in FIG. 7, a larger, conventional handle can also be used with the present invention to increase the ease of use of the surgical snare 2. This larger handle can be removable so as to allow the retrieval catheter 30 to be fed over the surgical snare 2 once the medical device 9 has been captured.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A surgical snare, comprising:
an operating wire;
an outer sheath comprising a lumen extending therethrough, the operating wire disposed within the lumen; and
a frictional locking member operably coupled to the outer sheath;
wherein the frictional locking member is configured to prevent longitudinal movement of the operating wire with respect to the outer sheath when no inwardly directed radial force is applied to an external surface of the frictional locking member;
wherein the operating wire is configured to be longitudinally movable within the outer sheath when the inwardly directed radial force is applied to the external surface of the frictional locking member, wherein the frictional locking member is actuated by the inwardly directed radial force applied to the external surface of the frictional locking member.

2. The surgical snare of claim 1, wherein:
the operating wire comprises an expandable loop at a distal end of the operating wire.

3. The surgical snare of claim 2, wherein:
the expandable loop comprises an engaged state and a released state, wherein the expandable loop in the released state has a larger circumference than when the expandable loop is in the engaged state.

4. The surgical snare of claim 1, further comprising:
a handle attached to a proximal end of the operating wire.

5. The surgical snare of claim 4, wherein:
the handle comprises a removably attached handle.

6. The surgical snare of claim 1, further comprising:
a retrieval catheter comprising a catheter lumen, wherein the outer sheath and frictional locking member are movably disposed within the catheter lumen.

7. The surgical snare of claim 1, wherein:
longitudinal movement of the operating wire with respect to the outer sheath is limited by frictional forces between the frictional locking member and the operating wire when no external force is applied.

8. The surgical snare of claim 1, wherein:
the frictional locking member is permanently attached to the outer sheath.

9. The surgical snare of claim 1, wherein:
the frictional locking member comprises a helical wire wrapped around a flexible tubing.

10. The surgical snare of claim 1, wherein:
the frictional locking member comprises a rigid tube, wherein the rigid tube comprises at least one crimp.

11. The surgical snare of claim 1, wherein:
the frictional locking member is integrally formed with the outer sheath.

12. A retrieval device, comprising:
a retrieval member;
a tube comprising a channel therethrough, the channel receiving the retrieval member; and
a fastening member operably coupled to the tube;

wherein the fastening member frictionally engages with the retrieval member, thereby preventing longitudinal movement of the retrieval member along the channel of the tube when no external force is applied to an external surface of the fastening member, and wherein the fastening member is configured to permit longitudinal movement of the retrieval member when an inwardly directed external radial force is applied to the external surface of the fastening member.

13. The retrieval device of claim 12, further comprising:
a handle attached to a proximal end of the tube.

14. The retrieval device of claim 12, further comprising:
a catheter comprising a lumen, wherein the tube and the fastening member are disposed within the lumen.

15. The retrieval device of claim 12, wherein:
the fastening member comprises a wire wrapped around a flexible tube, wherein the flexible tube is disposed around the retrieval member, the fastening member further comprising a shrink wrap tube disposed around the wire.

16. The retrieval device of claim 12, wherein:
the fastening member comprises a stiff tubing disposed circumferentially around the retrieval member, wherein the stiff tubing comprises at least one ridge.

17. A method for retrieving a medical device, comprising:
providing a surgical snare comprising an operating wire having an expandable loop at a distal end of the operating wire, an outer sheath comprising a lumen extending therethrough, the operating wire disposed within the lumen and longitudinally movable within the lumen, and a locking member operably coupled to the outer sheath, wherein the locking member is configured to permit the expandable loop of the operating wire to move between an engaged state and a released state when the locking member is actuated;
inserting the surgical snare into a patient's body;
advancing the surgical snare into the patient's body until a distal end of the surgical snare is adjacent to the medical device;
placing the expandable loop in a released state by applying an inwardly directed radial force to an external surface of the locking member to thereby allow the outer sheath to slide in a proximal direction relative to the operating wire until the expandable loop is moved to the released state;
positioning the expandable loop around the medical device; and
securing the expandable loop around the medical device by sliding the outer sheath in a distal direction relative to the operating wire until the expandable loop is in an engaged state, wherein the expandable loop has a smaller circumference while in the engaged state than when the expandable loop is in the released state, wherein the inwardly directed radial force is removed from the external surface of the looking member to thereby allow the locking member to frictionally engage the operating wire and thereby maintain the expandable loop in the engaged state.

18. The method of claim 17, further comprising:
retracting the surgical snare and the medical device from the patient's body.

19. The method of claim 17, further comprising:
providing a retrieval sheath comprising a retrieval sheath lumen;
feeding the retrieval sheath over the surgical snare by placing the surgical snare within the retrieval sheath lumen until the medical device is within a distal portion of the retrieval sheath lumen; and
retracting the surgical snare and the medical device through the retrieval sheath lumen from the patient's body.

20. The method of claim 19, wherein:
the surgical snare further comprises a handle removably attached to a proximal end of the outer sheath; and
further comprising removing the handle from the surgical snare prior to the step of feeding the retrieval sheath over the surgical snare.

\* \* \* \* \*